United States Patent
Al-Hammad et al.

(10) Patent No.: US 11,697,629 B2
(45) Date of Patent: Jul. 11, 2023

(54) SYSTEM AND PROCESS FOR METHANOL RECOVERY

(71) Applicant: SABIC Global Technologies B.V., Bergen op Zoom (NL)

(72) Inventors: Ali Al-Hammad, Riyadh (SA); Ijaz Chaudary, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/639,951

(22) PCT Filed: Aug. 10, 2018

(86) PCT No.: PCT/IB2018/056062
§ 371 (c)(1),
(2) Date: Feb. 18, 2020

(87) PCT Pub. No.: WO2019/038627
PCT Pub. Date: Feb. 28, 2019

(65) Prior Publication Data
US 2020/0247737 A1  Aug. 6, 2020

Related U.S. Application Data

(60) Provisional application No. 62/549,069, filed on Aug. 23, 2017.

(51) Int. Cl.
C07C 29/80 (2006.01)
C07C 29/151 (2006.01)

(52) U.S. Cl.
CPC .......... C07C 29/80 (2013.01); C07C 29/1518 (2013.01)

(58) Field of Classification Search
CPC ............................ C07C 29/80; C07C 29/1518
See application file for complete search history.

(56) References Cited

U.S. PATENT DOCUMENTS

| | | | | |
|---|---|---|---|---|
| 3,597,465 A | * | 8/1971 | Karafian | C01B 3/384 518/704 |
| 4,210,495 A | | 7/1980 | Pinto | 203/22 |
| 4,455,394 A | * | 6/1984 | Pinto | C07C 29/1518 518/703 |
| 4,592,806 A | | 6/1986 | Ilgner et al. | |
| 4,744,869 A | * | 5/1988 | Saito | C07C 29/80 203/84 |
| 5,449,440 A | | 9/1995 | Rescalli et al. | 203/20 |
| 5,998,489 A | * | 12/1999 | Kobayashi | C07C 29/1518 518/704 |
| 6,258,860 B1 | | 7/2001 | Weedon et al. | 518/706 |
| 2005/0107481 A1 | * | 5/2005 | Janssen | C07C 1/20 518/726 |

FOREIGN PATENT DOCUMENTS

| | | |
|---|---|---|
| DE | 3220995 A1 | 12/1983 |
| EP | 0040481 A2 | 11/1981 |
| EP | 0120269 A2 | 10/1984 |
| WO | WO-2010026412 A1 * 3/2010 | C07C 29/80 |

OTHER PUBLICATIONS

International Search Report and Written Opinion from PCT/IB2018/056062 dated Oct. 31, 2018, 9 pages.

* cited by examiner

Primary Examiner — Rosalynd A Keys
(74) Attorney, Agent, or Firm — Norton Rose Fulbright US LLP

(57) ABSTRACT

Certain embodiments are directed to methods of purifying methanol comprising fractionating a feed source into methanol and heavy alcohol or fusel alcohol fractions and further recovering methanol from the fusel alcohol fraction.

12 Claims, 1 Drawing Sheet

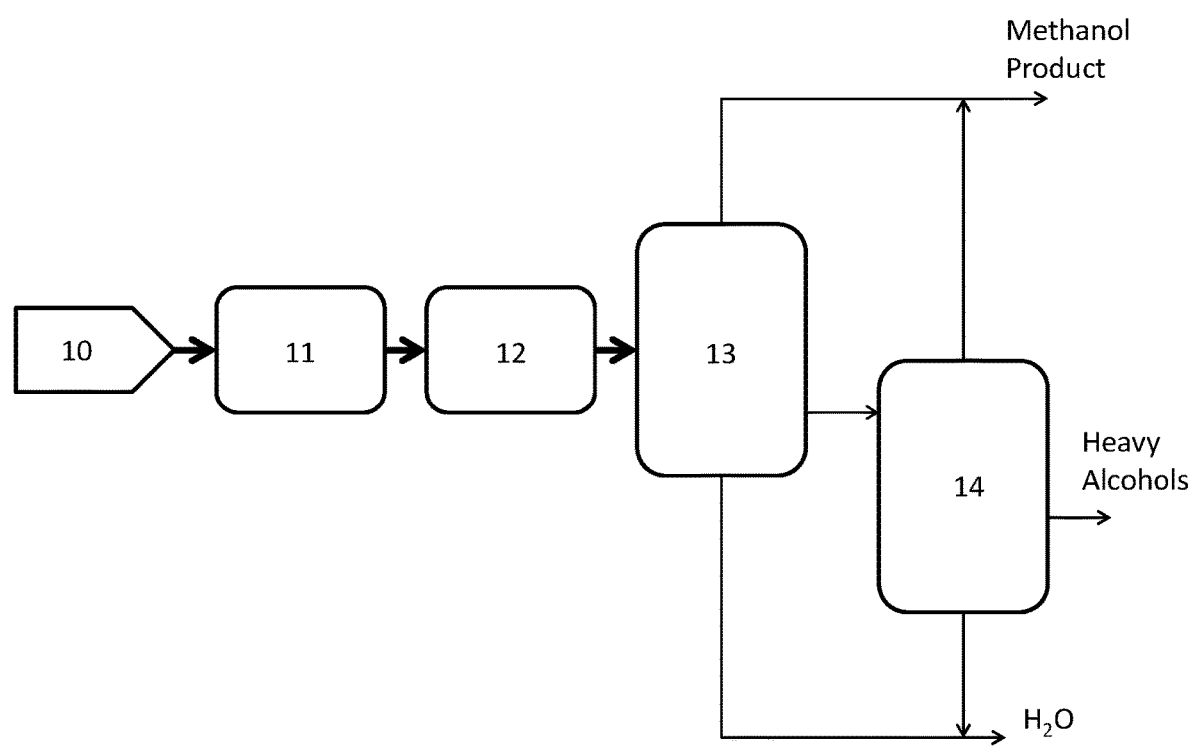

SYSTEM AND PROCESS FOR METHANOL RECOVERY

CROSS REFERENCE TO RELATED APPLICATIONS

This application is a national phase application under 35 U.S.C. § 371 of International Application No. PCT/IB2018/056062 filed Aug. 10, 2018, which claims priority to U.S. Provisional Patent Application No. 62/549,069 filed Aug. 23, 2017. The entire contents of each of the above-referenced disclosures is specifically incorporated by reference herein without disclaimer.

BACKGROUND OF THE INVENTION

A. Field of the Invention

The invention generally concerns composition, methods, and/or processes for the purification of methanol.

B. Description of Related Art

Methanol production processes are well-known. The methanol process typically comprises a reformer section, a synthesis section and a distillation section. In the reformer section, carbonaceous feedstock, such as natural gas, naphtha, or other oil fraction, is converted into a mixture of carbon oxides and hydrogen. Such a mixture of gases is often referred to as synthesis gas. The conversion of a hydrocarbon-containing feedstock into synthesis gas can be performed by steam reforming, by partial oxidation, by secondary/autothermal reforming, or by a combination of two or more of these processes. The synthesis step can be carried out by contacting the synthesis gas with a suitable methanol synthesis catalyst under an elevated synthesis gas pressure, typically in the range of from about 30 bar up to about 100 bar, more usually in the range of from about 50 bar up to about 100 bar, and at an elevated methanol synthesis temperature, typically from about 210° C. to about 270° C. or higher, e.g. up to about 300° C. As an example of a suitable methanol synthesis catalyst there can be mentioned a catalyst comprising a reduced zinc oxide/copper oxide mixture.

In the distillation section, the crude methanol produced during the synthesis step is transferred to the distillation section, in which the heavy alcohol byproducts are separated out and a purified methanol product is produced. One drawback of previously available technologies is that the heavy alcohol byproduct stream contains methanol. The current invention describes systems and methods for recovery of methanol from the heavy alcohol byproduct stream.

SUMMARY OF THE INVENTION

Certain embodiments are directed to methods of purifying methanol. The methods can include one or more steps that include (i) passing a feed stream comprising crude methanol through a first column; (ii) distributing a first purified methanol fraction to a top portion of the first column; (iii) distributing a first water fraction to a bottom portion of the first column; (iv) distributing a first waste alcohol fraction to a middle portion of the first column; (v) withdrawing the first waste alcohol fraction from the middle portion of the first column and passing the first waste alcohol fraction through a second column; (vi) distributing a second purified methanol fraction to a top portion of the second column; (vii) distributing a second water fraction to a bottom portion of the second column; (viii) distributing a second waste alcohol fraction to a middle portion of the second column; and (ix) withdrawing the second purified methanol from the top portion of the second column.

In certain aspects the source of the feed stream is the product of a methanol production process. The methanol synthesis feed stream can be produced by the reforming of natural gas. The methanol production process comprises synthesizing methanol by contacting synthesis gas with a catalyst, wherein the catalyst comprises zinc, copper, aluminum, or a combination comprising at least one of the foregoing. The crude methanol can comprise 50 to 70% methanol. In certain aspects the first waste alcohol fraction produced by the first column comprises 5 to 30% methanol. In certain aspects the purified methanol comprises greater than or equal to 90, 95, 98, or 99% methanol, and preferably greater than or equal to 99% methanol. In certain aspects the first and second columns are distillation columns. In certain aspects the temperature within both the first and second column is greater than 100° C., and particularly about 120° C. to 130° C. In certain aspects the operating pressure within the first column and the second column can be about 1 to 2 bar. In certain aspects the method further includes the step of withdrawing the first purified methanol fraction from the top portion of the first column. In certain aspects the first purified methanol fraction is combined with the second purified methanol fraction. In certain aspects the method further includes the step of withdrawing the first water fraction from the bottom portion of the first column and the second water fraction from the bottom portion of the second column. In embodiments the method further includes the step of combining the first water fraction withdrawn from the first column with the second water fraction withdrawn from the second column. In certain aspects the method includes the step of withdrawing a second waste alcohol fraction from the middle portion of the second column. In certain aspects the method further includes the step of passing the second waste alcohol fraction through a third column. In certain aspects the method includes the step of recycling the second waste alcohol fraction back to the first column.

Certain embodiments are directed to methods of purifying methanol, the methods including the steps of (i) passing a feed stream comprising crude methanol through a first column, wherein the crude methanol comprises 50 to 70% methanol; (ii) distributing a first purified methanol fraction to a top portion of the first column and withdrawing the first purified methanol fraction from the top portion of the first column; (iii) distributing a first water fraction to a bottom portion of the first column; (iv) distributing a first waste alcohol fraction to a middle portion of the first column, wherein the first waste alcohol fraction comprises 5 to 30% methanol; (v) withdrawing the first waste alcohol fraction from the middle portion of first column and passing the first waste alcohol fraction through a second column; (vi) distributing a second purified methanol fraction to a top portion of the second column; (vii) distributing a second water fraction to a bottom portion of the second column; (viii) distributing a second waste alcohol fraction to a middle portion of the second column; (ix) withdrawing the second waste alcohol fraction and recycling the second waste alcohol fraction back to the first column; and (x) withdrawing the second purified methanol fraction from the top portion of the second column; wherein the second purified methanol fraction comprises greater than or equal to 99% methanol. In certain aspects the source of the feed stream is the product of a methanol production process. In certain aspects the methanol production process comprises the reforming of natural gas.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other embodiments of the invention are discussed throughout this application and will become apparent from the following detailed description. Any embodiment discussed with respect to one aspect of the invention applies to other aspects of the invention as well and vice versa. Each embodiment described herein is understood to be embodiments of the invention that are applicable to all aspects of the invention. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 1 is a schematic diagram representing a methanol recovery system/process.

DETAILED DESCRIPTION OF THE INVENTION

In a conventional methanol production plant there are several streams that are considered to be byproduct or waste gas streams from the process. These byproduct or waste streams can be discharged to a fuel gas system. There are byproduct streams that contain significant quantities of methanol. These byproduct streams include a heavy byproduct/heavy alcohol stream containing some methanol, often described as fusel alcohols. Some amount of methanol is lost in the waste streams. It is generally considered uneconomic to recover the methanol from these byproduct streams.

Certain aspects of the invention can include converting a feedstock into a synthesis gas comprising hydrogen and at least one carbon oxide selected from carbon monoxide, carbon dioxide, and mixtures thereof; performing a methanol synthesis by supplying a synthesis gas to a first methanol synthesis reactor containing an appropriate methanol synthesis catalyst and operating the reactor under methanol synthesis conditions including appropriate synthesis temperature and pressure; recovering a methanol product stream comprising crude methanol, i.e., a crude methanol stream; separating the crude methanol stream into at least a methanol product stream and a byproduct stream; further recovering methanol from the byproduct stream that is separating the byproduct stream into a methanol stream and a non-methanol stream; and collecting a methanol product from the first and second separations.

In certain aspects the feedstock is natural gas that is converted to a synthesis gas by a process selected from steam reforming, partial oxidation, secondary/autothermal reforming, and a combination of two or more thereof.

The byproduct stream or fusel stream can be separated providing an overhead methanol product stream, a sidearm byproduct, and a bottom fraction comprising water.

Typically a methanol synthesis catalyst is a reduced zinc oxide/copper oxide catalyst. Suitable methanol synthesis conditions includes, but is not limited to use of a temperature of from about 210° C. to about 300° C. or about 210° C. to about 270° C., and a pressure of from about 30 bar to about 100 bar, or about 50 bar to about 100 bar.

The process enables recovery of methanol from the byproduct stream from the separation of a crude methanol stream. The methanol produced by separation of the byproduct stream can be collected with the methanol stream from the crude methanol stream separation.

It will be appreciated that, since the drawings are diagrammatic/schematic, further items of equipment such as heat exchangers, compressors, reflux drums, pumps, vacuum pumps, temperature sensors, pressure sensors, pressure relief valves, control valves, flow controllers, level controllers, holding tanks, storage tanks, and the like may be required. The provision of such ancillary items of equipment forms no part of the present invention and is in accordance with conventional chemical engineering practice.

Referring to FIG. 1, natural gas or other feedstock 10 is supplied to reformer 11 for the production of synthesis gas. Synthesis gas (e.g., a mixture of carbon monoxide, carbon dioxide, hydrogen and methane) is then supplied to methanol synthesis reactor 12, which under appropriate conditions produces crude methanol from the synthesis gas. Methanol synthesis reactor can be maintained at a temperature and pressure that results in the catalytic conversion of synthesis gas to crude methanol. Typical methanol synthesis conditions include, but are not limited to pressures in the region of 60 to 100 bar and an outlet temperature of from about 240° C. to about 300° C. when using a copper/zinc catalyst.

The crude methanol stream produced by methanol synthesis reactor 12 is provided to methanol separator 13. In certain aspects methanol separator 13 is a methanol distillation column. Methanol separator 13 produces an overhead methanol fraction (methanol product stream), a sidearm byproduct fraction (byproduct stream) and a bottom $H_2O$ fraction (water stream). The methanol product stream is condensed and recovered. In certain aspects the crude methanol is distilled at a reboiler temperature of about 125 to 130° C. at 1.3 to 1.8 bar with refined methanol being removed overhead at about 82° C. and by product stream being removed mid-column at about 104° C.

The byproduct stream is then introduced to second separator 14 that produces an overhead methanol fraction (methanol product stream), a sidearm byproduct fraction (heavy stream) and a bottom H₂O fraction (water stream). The methanol product stream condensed and recovered and can be combined with the methanol product stream from separator 13. The water stream of separator 13 and/or 14 are discharged for effluent treatment. In certain aspect the product methanol is at a purity of greater than 90, 95, 98, or 99%.

The invention claimed is:

1. A method of purifying methanol, comprising:
    passing a feed stream comprising crude methanol through a first column;
    distributing a first purified methanol fraction to a top portion of the first column;
    distributing a first water fraction to a bottom portion of the first column;
    distributing a first waste alcohol fraction to a middle portion of the first column;
    withdrawing the first waste alcohol fraction from the middle portion of the first column and passing the first waste alcohol fraction through a second column;
    distributing a second purified methanol fraction to a top portion of the second column;
    distributing a second water fraction to a bottom portion of the second column;
    distributing a second waste alcohol fraction to a middle portion of the second column;
    withdrawing the second purified methanol fraction from the top portion of the second column;
    withdrawing the first water fraction from the first column;
    withdrawing the second water fraction from the second column;
    combining the first water fraction withdrawn from the first column with the second water fraction withdrawn from the second column;
    passing a portion of the second waste alcohol fraction through a third column;
    condensing and recovering all of the first purified methanol fraction;
    withdrawing the second waste alcohol fraction; and
    recycling a portion of the second waste alcohol fraction back to the first column;
    wherein a pressure within the first column and the second column is about 1 bar to 2 bar;
    wherein a temperature within the first column and the second column is 120° C. to 130° C.;
    wherein a source of the feed stream is a product of a methanol production process; and
    wherein the methanol production process comprises synthesizing methanol by contacting synthesis gas with a catalyst.

2. The method of claim 1, wherein the catalyst comprises copper, zinc or a combination thereof.

3. The method of claim 2, wherein the methanol production process comprises the reforming of natural gas.

4. A method of purifying methanol, comprising:
    passing a feed stream comprising crude methanol through a first column;
    distributing a first purified methanol fraction to a top portion of the first column;
    distributing a first water fraction to a bottom portion of the first column;
    distributing a first waste alcohol fraction to a middle portion of the first column;
    withdrawing the first waste alcohol fraction from the middle portion of the first column and passing the first waste alcohol fraction through a second column;
    distributing a second purified methanol fraction to a top portion of the second column;
    distributing a second water fraction to a bottom portion of the second column;
    distributing a second waste alcohol fraction to a middle portion of the second column;
    withdrawing the second purified methanol fraction from the top portion of the second column;
    withdrawing the first water fraction from the first column;
    withdrawing the second water fraction from the second column;
    combining the first water fraction withdrawn from the first column with the second water fraction withdrawn from the second column;
    condensing and recovering the first purified methanol fraction;
    withdrawing the second waste alcohol fraction;
    passing a portion of the second waste alcohol fraction through a third column; and
    recycling a portion of the second waste alcohol fraction back to the first column;
    wherein a temperature within the first column and the second column is 120° C. to 130° C.;
    wherein a source of the feed stream is a product of a methanol production process;
    wherein the methanol production process comprises synthesizing methanol by contacting synthesis gas with a catalyst; and
    wherein the catalyst comprises aluminum.

5. The method of claim 2, wherein the catalyst is a reduced zinc oxide/copper oxide catalyst.

6. The method of claim 1, wherein the first waste alcohol fraction produced by the first column comprises 5 to 30% methanol.

7. The method of claim 1, wherein the second purified methanol fraction comprises greater than or equal to 99% methanol.

8. The method of claim 1, wherein the first column and the second column are distillation columns.

9. The method of claim 1, wherein a pressure within the first column and the second column is about 1 bar.

10. The method of claim 1, further comprising withdrawing the first purified methanol fraction from the top portion of the first column.

11. The method of claim 10, further comprising combining the first purified methanol fraction with the second purified methanol fraction.

12. The method of claim 1, wherein a pressure within the first column and the second column is 2 bar.

* * * * *